(12) United States Patent
Miyamoto

(10) Patent No.: US 8,552,038 B2
(45) Date of Patent: Oct. 8, 2013

(54) CRYSTALLINE FORMS OF THIAZOLIDINEDIONE COMPOUND AND ITS MANUFACTURING METHOD

(75) Inventor: Hiroshi Miyamoto, Koto (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/465,202

(22) Filed: May 7, 2012

(65) Prior Publication Data

US 2012/0252854 A1    Oct. 4, 2012

Related U.S. Application Data

(62) Division of application No. 12/311,610, filed as application No. PCT/JP2008/052594 on Feb. 8, 2008, now Pat. No. 8,236,834.

(60) Provisional application No. 60/900,251, filed on Feb. 8, 2007.

(51) Int. Cl.
    A61K 31/427    (2006.01)
    C07D 277/34    (2006.01)

(52) U.S. Cl.
    USPC .......................................... 514/369; 548/183

(58) Field of Classification Search
    USPC .......................................... 548/183; 514/369
    See application file for complete search history.

(56) References Cited

U.S. PATENT DOCUMENTS

| 6,432,993 B1 | 8/2002 | Fujita et al. |
| 6,562,849 B1 | 5/2003 | Fujita et al. |
| 7,816,552 B2 | 10/2010 | Kajino et al. |
| 2003/0101925 A1 | 6/2003 | Ohnota et al. |

(Continued)

FOREIGN PATENT DOCUMENTS

| JP | 2003-238406 | * | 8/2003 | ........... C07D 277/34 |
| JP | 2003-238406 A | | 8/2003 | |

(Continued)

OTHER PUBLICATIONS

D.J.W. Grant, "Theory and Origin of Polymorphism", chapter 1, pp. 1 to 10 and J.K. Guillroy, "Generation of Polymorphs, Hydrates, Solvates, and Amorphous Solids", chapter 5, pp. 183 to 226, *Polymorphism in Pharmaceutical Solids*, edited by H.G. Brittan (1999).

(Continued)

*Primary Examiner* — Kamal Saeed
*Assistant Examiner* — Janet L Coppins
(74) *Attorney, Agent, or Firm* — Holtz Holtz Goodman & Chick PC

(57) ABSTRACT

A crystalline form of a hydrate of a dihydrochloride 5-(4-{[6-(4-amino-3,5-dimethylphenoxy)-1-methyl-1-H-benzimidazol-2-yl]methoxy}benzyl)-1,3-thiazolidine-2,4-dione represented by the following formula:

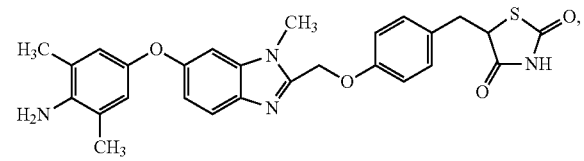

wherein the crystalline form shows main peaks at interplanar spacings of 10.42, 5.85, 5.52, 3.84, 3.46 and 2.95 angstroms in X-ray powder diffraction obtained with Cu Kα line radiation (wavelength λ=1.54 angstroms).

23 Claims, 5 Drawing Sheets

(56) References Cited

U.S. PATENT DOCUMENTS

| | | |
|---|---|---|
| 2009/0028868 A1 | 1/2009 | Fujiwara et al. |
| 2011/0124692 A1 | 5/2011 | Kajino et al. |
| 2011/0160462 A1 | 6/2011 | Kajino et al. |

FOREIGN PATENT DOCUMENTS

| | | |
|---|---|---|
| JP | 2004-075448 A | 3/2004 |
| JP | 2004-083574 A | 3/2004 |
| JP | 2005-162727 A | 6/2005 |
| RU | 2 196 141 C2 | 1/2003 |
| WO | WO 2004/083167 A1 | 9/2004 |

OTHER PUBLICATIONS

S. Byrn, et al. "Pharmaceutical Solids: A Strategic Approach to Regulatory Considerations", *Pharmaceutical Research*, vol. 12, No. 7, pp. 945 to 954 (1995).
Israeli Office Action, Israeli Patent Application No. 197826, issued on Aug. 30, 2012.
Colombian Office Action dated Apr. 4, 2013 (including an English-language translation thereof) in Colombian Patent Application No. 0941703.
Mino R. Caira, "Crystalline Polymorphism of organic compound," Topics in Current Chemistry, Springer, Berlin, De., vol. 198, Jan. 1, 1998, pp. 163-208.
Examination Report from EPO dated Aug. 16, 2011.
The first Office Action in China, dated Feb. 24, 2011 for Chinese Patent Appl. No. 200860001045.
A letter dated Aug. 21, 2009 from the patent agent in Pakistan, reporting the contents of the first Office Action from the Patent Office in Pakistan (the second half of the letter with their comments has been omitted) for Pakistan Patent Appl. No. 0118/2008.
The first Examination Report issued by the Russian Patent Office in Russian Appln. No. 2009115179 dated May 11, 2010, and translation thereof into English.
The first Examination Report from the Intellectual Property Corporation of Malaysia dated Aug. 30, 2010 for Malaysian Patent Appl. No. PI 20091505.
The first and second Examination Reports issued by IP Australia dated Sep. 13, 2010 and May 3, 2011 for Australian Patent Appl. No. 2008215384.
The first Examination Report dated Sep. 24, 2010 from the Intellectual Property Office of New Zealand for New Zealand Patent Appl. No. 575786.
The first Examination Report dated Jul. 6, 2010 from the Canadian Intellectual Property Office (the second Examination Report did not refer to any citations) for Canadian Patent Appl. No. 2,665,048.
The first Examination Report issued on behalf of the Intellectual Property Office of Singapore by letter of Dec. 30, 2010 for Singapore Patent Appl. No. 200902209-6.
Peruvian Office Action entitled "Technical Report PCG 49-2011", May 20, 2011.
Shibata Tomoyuki et al: "Preparation of sulfamide derivatives as antitumoral agents", Database CA, Chemical Abstracts Service, XP-002485467.
International Search Report dated Oct. 7, 2008 for PCT/JP2008/052594.

* cited by examiner

CRYSTALLINE FORMS OF THIAZOLIDINEDIONE COMPOUND AND ITS MANUFACTURING METHOD

CROSS-REFERENCE TO RELATED APPLICATIONS

This application is a divisional application of application Ser. No. 12/311,610 filed Apr. 6, 2009 (U.S. Pat. No. 8,236,834), which is the United States national phase application under 35 USC 371 of International application PCT/JP2008/052594 filed Feb. 8, 2008. U.S. Ser. No. 12/311,610 and PCT/JP2008/052594 are incorporated by reference herein in their entirety. Priority is claimed under 35 USC 119(e) of U.S. provisional application Ser. No. 60/900,251 filed Feb. 8, 2007.

BACKGROUND OF THE INVENTION

1. Field of the Invention

The present invention relates to crystalline forms of a thiazolidinedione compound having a significant ability of peroxisome proliferator-activated receptor (PPAR) γ activation, a significant anticancer activity and favorable properties for manufacturing medicaments, as well as being highly pure and excellent in preservation stability and handleability, manufacturing methods thereof, and medicines containing as an active component the crystalline forms of the thiazolidinedione compound (in particular, PPARγ activators or anticancer pharmaceutical compositions).

2. Description of the Related Art

Japanese Patent No. 3488099 (International Patent Application Laid-Open No. 99/18081, U.S. Pat. No. 6,432,993, European Patent No. 1022272) (Patent Literature 1), Japanese Patent Laid-Open No. 2003-238406 (International Patent Application Laid-Open No. WO03/053440) (Patent Literature 2), Japanese Patent Laid-Open No. 2004-083574 (WO2004/000356) (Patent Literature 3), Japanese Patent Laid-Open No. 2005-162727 (WO2004/083167) (Patent Literature 4), and International Patent Application Laid-Open No. 2007/091622 (Patent Literature 5) disclose a thiazolidinedione compound represented by the after-mentioned formula (I) (abbreviated as Compound (I) hereinafter.). Compound (I) has a significant ability of peroxisome proliferator-activated receptor (PPAR) γ activation and is expected to exert its availability as a PPARγ activator or an anticancer pharmaceutical composition.

In general, substances used in pharmaceutical products are required to have high purity to avoid unexpected adverse effects caused by impurities of the substances. The impurities include by-products (analog substances) being produced during the manufacture of the pharmaceutical ingredients themselves, raw materials and solvents being used for manufacturing the pharmaceutical ingredients and the like. Also, the substances are required to have more favorable physical and chemical properties for manufacturing medicaments such as crystal forms of pharmaceutical ingredients which are resistant to a heat treatment step and the like for preparation, or high solubility which makes pharmaceutical ingredients able to increase their absorbability so that they can exert their effects at lower doses. Moreover, it is important that the pharmaceutical ingredients can be stored for long periods of time, while maintaining the quality. In addition, large-scale refrigerating installations are needed to maintain the quality of pharmaceutical ingredients if they are required to be stored at low temperatures. Therefore, it is industrially significant to find crystalline forms which are stable and such as can be stored at room temperature or even higher temperatures.

As mentioned above, an industrial and large-scale manufacturing method is required to manufacture pharmaceutical ingredients being more highly pure, having favorable properties for manufacturing medicaments and being stockable while stably maintaining their purity and properties for long periods of time.

[Patent Literature 1] Japanese Patent No. 3488099 (Pamphlet of International Patent Application Laid-Open No. 99/18081, Specification of U.S. Pat. No. 6,432,993, Specification of European Patent No. 1022272)

[Patent Literature 2] Japanese Patent Laid-Open No. 2003-238406 (Pamphlet of international Patent Application Laid-Open No. WO03/053440)

[Patent Literature 3] Japanese Patent Laid-Open No. 2004-083574 (Pamphlet No. WO2004/000356)

[Patent Literature 4] Japanese Patent Laid-Open No. 2005-162727 (Pamphlet No. WO2004/083167)

[Patent Literature 5] Pamphlet of International Patent Application Laid-Open No. 2007/091622

The present inventors have done earnest research on Compound (I) which has a significant ability of peroxisome proliferator-activated receptor (PPAR) γ activation and is expected to exert its availability as a PPAR γ activator or an anticancer pharmaceutical composition. As a result, the inventors found novel crystalline forms of hydrates of the dihydrochloride of Compound (I) having significant physical and chemical properties as pharmaceutical ingredients, being excellent in preservation stability at room temperature as well as being highly pure, and manufacturing methods thereof. Based on this finding, the inventors have achieved the present invention.

SUMMARY OF THE INVENTION

The present invention relates to the followings:

(1) A crystalline form of a hydrate of a dihydrochloride of 5-(4-{[6-(4-amino-3,5-dimethylphenoxy)-1-methyl-1-H-benzimidazol-2-yl]methoxy}benzyl)-1,3-thiazolidine-2,4-dione represented by the following formula (I);

[Formula 1]

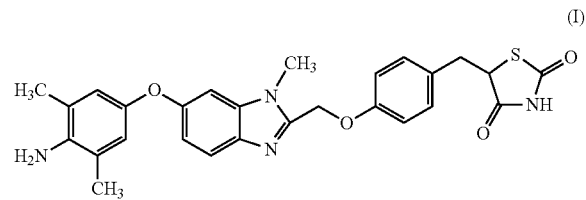

(2) The crystalline form of a hydrate of a dihydrochloride of 5-(4-{[6-(4-amino-3,5-dimethylphenoxy)-1-methyl-1-H-benzimidazol-2-yl]methoxy}benzyl)-1,3-thiazolidine-2,4-dione represented by the general formula (I) according to (1) above, wherein the crystalline form shows main peaks at interplanar spacings of 7.06, 5.79, 5.43, 4.44, 4.18, 3.97, 3.91, 3.68, 3.61, 3.48, 3.24 and 2.97 angstroms in X-ray powder diffraction obtained with Cu Kα line radiation (wavelength λ=1.54 angstroms) (Crystalline form A);

(3) The crystalline form of a hydrate of a dihydrochloride of 5-(4-{[6-(4-amino-3,5-dimethylphenoxy)-1-methyl-1-H-benzimidazol-2-yl]methoxy}benzyl)-1,3-thiazolidine-2,4-dione represented by the general formula (I) according to (1)

above, wherein the crystalline form shows main peaks at interplanar spacings of 10.42, 5.85, 5.52, 3.84, 3.46 and 2.95 angstroms in X-ray powder diffraction obtained with Cu Kα line radiation (wavelength λ=1.54 angstroms) (Crystalline form B);

(4) The crystalline form according to (2) above, wherein the impurity content ratio measured by HPLC is 2.00% or less;

(5) The crystalline form according to (2) above, wherein the impurity content ratio measured by HPLC is 1.50% or less;

(6) A pharmaceutical composition containing as an active component the crystalline form of a hydrate of the dihydrochloride of the thiazolidinedione compound represented by the general formula (I) according to any one of (1) to (5) above;

(7) A PPARγ activator containing as an active component the crystalline form of a hydrate of the dihydrochloride of the thiazolidinedione compound represented by the general formula (I) according to any one of (1) to (5) above;

(8) An anticancer pharmaceutical composition containing as an active component the crystalline form of a hydrate of the dihydrochloride of the thiazolidinedione compound represented by the general formula (I) according to any one of (1) to (5) above;

(9) A pharmaceutical composition for preventing or treating diabetes, containing as an active component the crystalline faith of a hydrate of the dihydrochloride of the thiazolidinedione compound represented by the general formula (I) according to any one of (1) to (5) above.

(10) A pharmaceutical composition for preventing or treating cancer when occurring in conjunction with diabetes, containing as an active component the crystalline form of a hydrate of the dihydrochloride of the thiazolidinedione compound represented by the general formula (I) according to any one of (1) to (5) above.

(11) A method of manufacturing the crystalline form according to (2) above, characterized in that 5-(4-{[6-(4-amino-3,5-dimethylphenoxy)-1-methyl-1-H-benzimidazol-2-yl]methoxy}benzyl)-1,3-thiazolidine-2,4-dione is formed into an aqueous solution thereof, and subsequently hydrochloric acid is dripped thereto;

(12) A method of manufacturing the crystalline form according to (2) above, characterized in that 5-(4-{[6-(4-amino-3,5-dimethylphenoxy)-1-methyl-1-H-benzimidazol-2-yl]methoxy}benzyl)-1,3-thiazolidine-2,4-dione is formed into an aqueous solution thereof, and subsequently hydrochloric acid is dripped thereto to give a crystalline form of a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride, which is further dissolved or slurried in water and then hydrochloric acid is dripped thereto; and

(13) A method of manufacturing the crystalline form according to (2) above, characterized in that 5-(4-{[6-(4-amino-3,5-dimethylphenoxy)-1-methyl-1-H-benzimidazol-2-yl]methoxy}benzyl)-1,3-thiazolidine-2,4-dione is formed into an aqueous solution thereof,
and subsequently hydrochloric acid is dripped thereto to give a crystalline form of a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride,
which is further dissolved or slurried in water,
and subsequently base is added thereto to give a solution or slurry,
and then hydrochloric acid is dripped thereto.

(14) A method of manufacturing the crystalline form according to (2) above, characterized in that 5-(4-{[6-(4-amino-3,5-dimethylphenoxy)-1-methyl-1-H-benzimidazol-2-yl]methoxy}benzyl)-1,3-thiazolidine-2,4-dione is formed into an aqueous solution thereof,
and subsequently seeds of a crystalline form of a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride are added while hydrochloric acid is dripped thereto.

(15) A method of manufacturing the crystalline form according to (2) above, characterized in that 5-(4-{[6-(4-amino-3,5-dimethylphenoxy)-1-methyl-1-H-benzimidazol-2-yl]methoxy}benzyl)-1,3-thiazolidine-2,4-dione is formed into an aqueous solution thereof,
and subsequently hydrochloric acid is dripped thereto to give a crystalline form of a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride,
which is further dissolved or slurried in water
and subsequently seeds of a crystalline form of a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride are added
while hydrochloric acid is dripped thereto.

(16) A method of manufacturing the crystalline form according to (2) above, characterized in that 5-(4-{[6-(4-amino-3,5-dimethylphenoxy)-1-methyl-1-H-benzimidazol-2-yl]methoxy}benzyl)-1,3-thiazolidine-2,4-dione is formed into an aqueous solution thereof,
and subsequently hydrochloric acid is dripped thereto to give a crystalline form of a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride,
which is further dissolved or slurried in water,
and subsequently base is added thereto to give solution or slurry,
and then seeds of a crystalline form of a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride are added
while hydrochloric acid is dripped thereto.

(17) A method of manufacturing the crystalline form according to (3) above, characterized in that a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride is crystallized from methanol.

The crystalline form of a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride represented by (I) above in the present invention (hereinafter may be abbreviated as the crystalline form in the present invention) is a solid whose internal structure is composed of constituent atoms (or the groups thereof) assembled into regularly structured 3-dimensional repeats. The crystalline form is distinguished from an amorphous solid, which has no such regularly structured internal structure.

Even a single compound can be formed into a number of different crystalline forms having different internal structures and physical and chemical properties (crystal polymorphs), depending on crystallization conditions. The crystalline form in the present invention may be any one of the crystal polymorphs or a mixture of two or more of the crystal polymorphs.

The crystalline form in the present invention may absorb water and have water adhere by leaving the same in the atmosphere. The crystalline form in the present invention may also absorb an organic solvent to form a solvate when mixed with the solvent. Moreover, the crystalline form in the present invention may form a hemihydrate and even an anhydrous form thereof by, for example, heating the same to between 25° C. and 150° C. under normal atmospheric conditions.

The crystalline form in the present invention includes the crystalline form with adhered water, a crystalline form composed of a hydrate or solvate thereof, a crystalline form containing a hemihydrate thereof and a crystalline form containing an anhydrous form thereof. Among these crystalline forms, as the crystalline form in the present invention, a crystalline form of a dihydrochloride monohydrate of Compound (I) is preferred.

As a form of the crystalline form in the present invention, can be included Crystalline form A, which shows main peaks at interplanar spacings of 7.06, 5.79, 5.43, 4.44, 4.18, 3.97, 3.91, 3.68, 3.61, 3.48, 3.24 and 2.97 angstroms in X-ray powder diffraction obtained with Cu Kα line radiation (wavelength $\lambda=1.54$ angstroms), wherein the main peaks are peaks which have relative intensities greater than 30% based on the intensity 100 of a peak at an interplanar spacing $d=7.06$ angstroms and peaks which are not observed in after-mentioned Crystalline form in the present invention.

The interplanar spacing d is calculated according to the equation: $2 d \sin \theta = n\lambda$, wherein n equals 1.

Another form of the crystalline form in the present invention is Crystalline form B, which shows main peaks at interplanar spacings of 10.42, 5.85, 5.52, 3.84, 346 and 2.95 angstroms in X-ray powder diffraction obtained with Cu Kα line radiation (wavelength $\lambda=154$ angstroms), wherein the main peaks are peaks which have relative intensities greater than 20% based on the intensity 100 of a peak at an interplanar spacing $d=3.46$ angstroms.

Furthermore, the above mentioned relative intensities of the main peaks may vary in accordance with differences in crystalline form growth fronts (crystal habits). Such crystalline forms are recognized as identical in terms of crystalline form and therefore included in the present invention.

In the present invention, the level of impurity contained in a crystalline form can be determined by conventional methods in analytic chemistry such as high-performance liquid chromatography (hereinafter may be abbreviated as HPLC), % by weight, and preferably the peak area ratio by using HPLC. Measurement conditions for HPLC may be arbitrarily selected. Preferred measurement conditions are described below.
HPLC Measurement Conditions (1)
Detector: UV absorptiometer (wavelength: 230 nm)
Column: Waters Corporation, XTerra $RP_{18}$ (4.6 mm×150 mm)
Column temperature: 40° C.
Mobile phase: 0.01 mol/ml ammonium acetate buffer-acetonitrile (65:35)
Flow rate: 1 ml/min (Under the present conditions, Compound (I) showed a retention time of approximately 25 minutes.)
Injection amount: 10 µl
Peak area measurement range: 70 minutes after the start of the injection
HPLC Measurement Conditions (2)
Detector: UV absorptiometer (wavelength: 230 nm)
Column: Waters Corporation, XTerra $RP_{18}$ (4.6 mm×150 mm)
Column temperature: 40° C.
Mobile phase: 0.01 mol/ml ammonium acetate buffer-acetonitrile (56:44)
Flow rate: 1 ml/min (Under the present conditions, Compound (I) showed a retention time of approximately 8 minutes.)
Injection amount: 10 µl
Peak area measurement range: 70 minutes after the peak which elutes next to the peak whose retention time relative to Compound (I) is 1.48.

Under HPLC Measurement Conditions (I), the peak area ratios are measured for Compound (1) and compounds which are impurities detected from 0 minute to 70 minutes. Under HPLC Measurement Conditions (2), the peak area ratios are measured for compounds which are impurities detected for 70 minutes after the peak which elutes next to the peak whose retention time relative to Compound (I) is 1.48.

The term peak for compounds which are impurities here represents all peaks whose peak area ratios are measured as 0.01% or more, excluding the peak for Compound (I) and the peak which is detected when injecting solvent alone.

In the present invention, the term impurity content ratio measured by HPLC represents the ratio of the integration area for all peaks whose peak area ratios are measured as 0.01% or more, excluding the peak for Compound (I) and the peak which is detected when injecting solvent alone, to the peak area for Compound (I) under the above mentioned conditions by using HPLC.

Among the crystalline forms in the present invention, with regard to Crystalline form A, the impurity content ratio measured by HPLC is preferably 2.00% or less, and more preferably 1.50% or less.

The crystalline forms in the present invention are highly pure, white in their color tone, and excellent in preservation stability, handleability and the like. Especially, Crystalline form A in the present invention has a low amount of residual solvent and is highly pure and white in its color tone, and excellent in preservation stability in the form of hydrate at room temperature because the dehydration temperature of the hydrate is high. Crystalline form B in the present invention has higher solubility than the Compound (I) which has been known. Taken together, the crystalline forms in the present invention are useful as materials for manufacturing medicines which are mass-produced in industrial production (in particular, PPARγ activators, agents for preventing and/or treating cancers, agents for preventing and/or treating diabetes, or agents for preventing and/or treating cancers when occurring in conjunction with diabetes).

Furthermore, the method of manufacturing the crystalline form in the present invention is a useful method for manufacturing materials for medicines which are mass-produced in industrial production, because the method can reduce the amount of residual solvent, manufacture a highly pure crystalline form, and produce a white crystalline form by decolorizing the crystalline form.

DETAILED DESCRIPTION OF THE PREFERRED EMBODIMENTS

Figure 1:
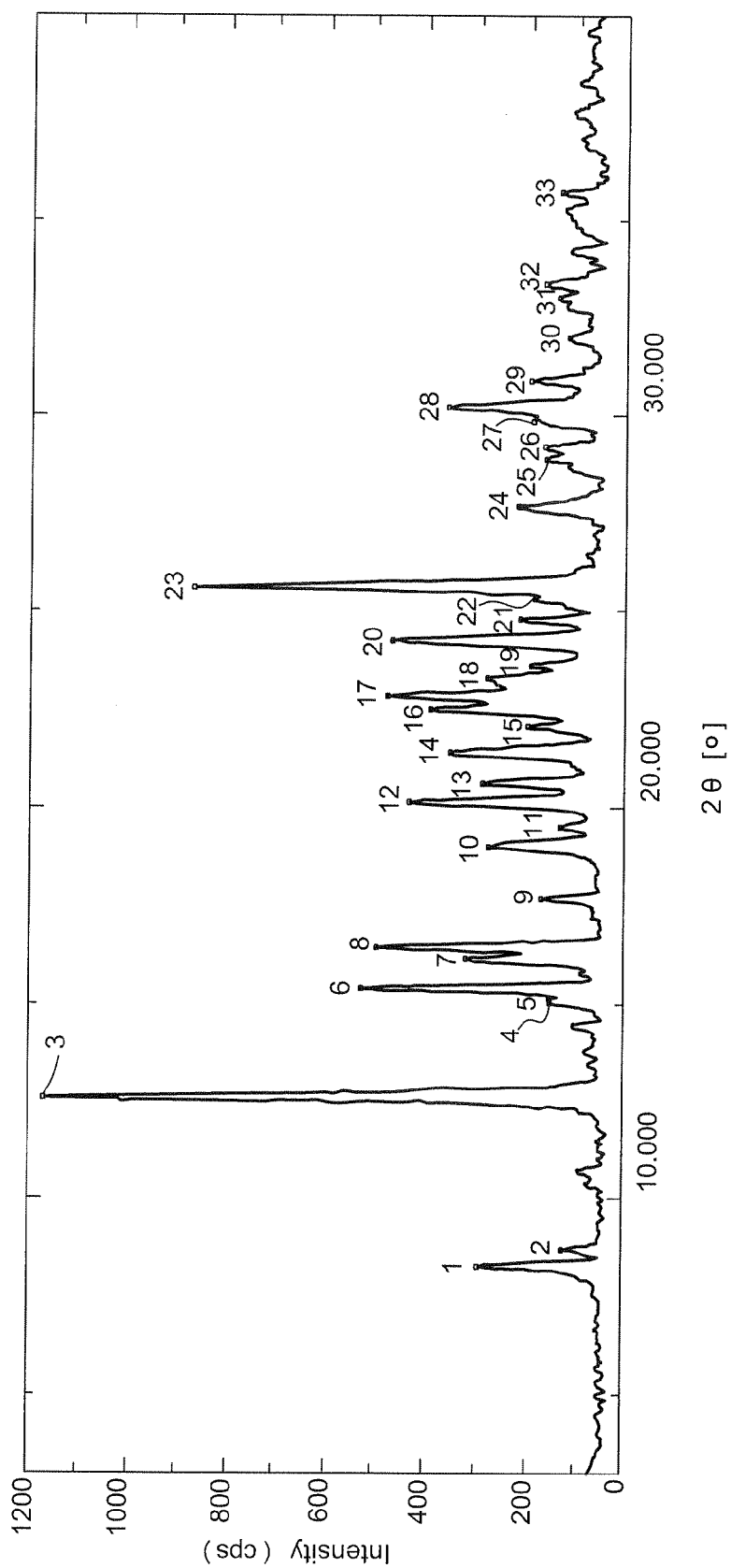
FIG. 1 is an X-ray powder diffraction pattern for Crystalline form A obtained in Example 1, the vertical axis showing diffraction intensity in units of counts/see (cps), and the horizontal axis showing values of diffraction angle 2θ.

The above mentioned Compound (I) can be manufactured by the method disclosed in Japanese Patent No. 3488099 or a method similar to that method.

The crystalline form in the present invention can be manufactured by dissolving Compound (I) or various salts of Compound (I) or various solvates thereof, the dihydrochloride of Compound (I) or various solvates thereof, or the hydrate of the dihydrochloride of Compound (I) itself in an adequate solvent, followed by desalination (neutralization), addition of hydrogen chloride or hydrochloric acid, concentration of the solution, cooling, mixing with a good solvent and a poor solvent and the like, which lead to supersaturation conditions to allow precipitation of the hydrate of the dihydrochloride of Compound (I), followed by isolation of the precipitated crystalline form. Moreover, a solution of synthetic crude products containing Compound (I) described above can be used as the solution in which Compound (I) or various salts of Compound (I) or various solvates thereof, the dihydrochloride of Compound (I) or various solvates thereof, or the hydrate of the dihydrochloride of Compound (I) itself is dissolved.

The precipitation of the crystalline form can be spontaneously initiated in a reaction container, but also can be initiated or promoted by giving mechanical stimulus thereto, such as seed crystalline form inoculation, ultrasonic stimulation and rubbing the surface of the reactor.

The obtained crystalline form can be subjected to recrystallization and slurry purification to further improve the purity and quality thereof.

In cases where various salts of Compound (I) or various solvates thereof are used, desalination (neutralization) may be performed in order to ensure obtainment of the dihydrochloride of Compound (I). In such cases, a base is generally used for desalination. Examples of the base are not limited as long as they can perform desalination but include alkali metal hydroxides such as lithium hydroxide, sodium hydroxide, potassium hydroxide or cesium hydroxide, alkali earth metal hydroxides such as magnesium hydroxide or calcium hydroxide, alkali earth metal oxides such as magnesium oxide or calcium oxide, or amines such as ammonia, methylamine, dimethylamine, trimethylamine, ethylamine, diethylamine, or tributylamine. Preferably, the base is an alkali metal hydroxide or an amine. More preferably, the base is lithium hydroxide, sodium hydroxide, potassium hydroxide, tributylamine or ammonia.

The base can be added either directly or after being dissolved in various solvents.

The amount of the base to be added is not limited but is generally in the range of 1 to 4 equivalents per equivalent of various salts of Compound (I).

In cases where hydrogen chloride or hydrochloric acid is added in order to crystallize the hydrate of the dihydrochloride of Compound (I), the amount thereof is preferably greater than the amount required for Compound (I) to form the dihydrochloride thereof and precipitate out as the crystalline form thereof. Moreover, the amount of hydrogen chloride or hydrochloric acid to be added is generally in the range of 0.1 to 20 equivalents and more preferably in the range of 2 to 10 equivalents per equivalent of Compound (I) in order to lower the solubility of the hydrate of the dihydrochloride of Compound (I) in solvents.

Examples of methods for concentrating the solution of Compound (I) or the hydrate of the dihydrochloride thereof include a concentration method which allows the solvent to evaporate by heating under atmospheric or reduced pressure by using a rotary evaporator or the like, or a concentration method using a reverse osmosis membrane. The reverse osmosis membrane to be used for condensing the solution may be selected from, for example, a polyacrylonitrile type membrane, a polyvinyl alcohol type membrane, a polyamide type membrane, a cellulose acetate type membrane and the like.

The temperature at which the hydrate of the dihydrochloride of Compound (I) is crystallized is generally in the range of −70 to 150° C., and preferably −70 to 100° C.

Examples of good solvents to be used to manufacture the crystalline form in the present invention include, for example, water, alcohols such as methanol or ethanol, ketones such as acetone or methylethylketone, ethers such as tetrahydrofuran or dioxane, nitriles such as acetonitrile or propionitrile, esters such as methyl acetate or ethyl acetate, amides such as dimethylformamide, dimethylacetamide or hexamethylphosphoric acid triamide, sulfoxides such as dimethylsulfoxide, or mixed solvents thereof. Preferably, methanol, tetrahydrofuran or mixed solvents thereof with water are used.

Poor solvents to be used to manufacture the crystalline form in the present invention are selected in accordance with the solvents being used as good solvents. Examples of the poor solvents include, for example, water, C2 to C4 alcohols such as ethanol, propanol and butanol, ketones such as acetone or methylethylketone, ethers such as diethyl ether, esters such as ethyl acetate and propyl acetate, and nitriles such as acetonitrile, propionitrile and butyronitrile.

In cases where Crystalline form A is to be obtained, Crystalline form A can be purified by forming an aqueous solution of Compound (I) (preferably, a mixed solution with tetrahydrofuran and water), and subsequently hydrochloric acid is dripped thereto to enhance the purity of the crystalline form.

After dissolving or slurrying the obtained Crystalline form A in water, hydrochloric acid may be dripped thereto to further enhance the purity thereof.

In such cases, the purification effect can be enhanced by addition of a base before starting the drip of hydrochloric acid in some cases. In cases where a base is added, examples of the base are not limited to but generally include inorganic bases such as lithium hydroxide, sodium hydroxide, potassium hydroxide, magnesium hydroxide and calcium hydroxide; and organic bases such as trimethylamine, triethylamine, diisopropylethylamine and tributylamine. Preferably, sodium hydroxide or potassium hydroxide is used.

The dissolution temperature or the slurry temperature in water is not limited but is generally in the range of 0 to 100° C. (reflux temperature), preferably in the range of 20 to 100° C. (reflux temperature), and more preferably in the range of 30 to 100° C. (reflux temperature).

The duration of dissolution or slurrying is not limited to but is generally in the range of 5 minutes to 12 hours, and preferably in the range of 10 minutes to 6 hours.

In the case of slurrying, the drip of hydrochloric acid after slurrying may be performed either after drying or without drying the crystalline form which is isolated after slurrying, or immediately after slurrying without isolation. Either way is acceptable.

The amount of hydrochloric acid to be used after dissolution or slurrying in water is not limited as long as it is greater than or equal to the amount required for Compound (I) to form the dihydrochloride thereof and precipitate out the crystalline form thereof. Hydrochloric acid is generally added until the resulting solution reaches a pH ranging from 2 to 0.5 in order to lower the solubility of Crystalline form A to water.

Crystalline form A may be added as a seed crystalline form either before starting the drip of hydrochloric acid or during the drip thereof. In cases where a seed crystalline form is added, the amount of the seed crystalline form to be added is not limited to but is generally in the range of 0.0001 to 20%, preferably 0.001 to 10%, and more preferably 0.01 to 5% relative to the amount of Crystalline form A to be purified.

The temperature at which hydrochloric acid is dripped is generally in the range of 0 to 100° C. (reflux temperature), preferably in the range of 20 to 100° C. (reflux temperature), and more preferably in the range of 50 to 100° C. (reflux temperature).

In cases where Crystalline form B in the present invention is to be obtained, the dihydrochloride of Compound (I) or the hydrate thereof is crystallized from methanol (preferably anhydrous methanol).

As a starting material for the manufacture of Crystalline form A in the present invention, Compound (I), various salts of Compound (I), various solvates thereof, the dihydrochloride of Compound (I) or various solvates of the dihydrochloride of Compound (I), or the hydrate of the dihydrochloride of Compound (I) which itself is already isolated may be used. Alternatively, a solution of synthetic crude products containing Compound (I) may be used because the product can be purified by crystallization. As a starting material for the manufacture of Crystalline form B in the present invention, the dihydrochloride of Compound (I) or the hydrate thereof is used.

Crystalline forms A or B which is precipitated out can be isolated by, for example, filtration, centrifugation or decantation and the like. The isolated crystalline form may be rinsed with an adequate solvent as required. To rinse the crystalline form in the present invention, solvents, for example, water; alcohols such as methanol, ethanol and isopropanol; ketones such as acetone; esters such as methyl formate, ethyl formate, methyl acetate and ethyl acetate; aromatic hydrocarbons such as toluene and xylene; nitriles such as acetonitrile; ethers such as diethylether and tetrahydrofuran, and mixed solvents thereof can be used. Preferably, water, methanol, tetrahydrofuran, or mixed solvents thereof are used.

The isolated crystalline form is dried generally in the range of 0 to 150° C., and preferably in the range of 20 to 90° C. until the weight remains almost constant. Drying of the crystalline form may be performed in the presence of drying agents such as silica gel or calcium chloride, or under reduced pressure as required. Under reduced pressure, the crystalline form can be dried without dehydrating the crystalline form water by regulating temperature and pressure. In such cases, the pressure is regulated to be relatively high for a high drying temperature. For example, in cases where Crystalline form A in the present invention is dried, the pressure is set in the range of 0.7 to 50 kPa, and preferably in the range of 1.8 to 11 kPa for the drying temperature at 50° C.

In cases where the dried crystalline form is dehydrated as a result of drying without regulating temperature and pressure, the dried crystalline form may be subjected to moisture absorption generally under the temperature range of 0 to 50° C. in 10 to 100% relative humidity range, and preferably under the temperature range 10 to 40° C. in 20 to 100% relative humidity range until the weight remains almost constant. The obtained crystalline form can be subjected to recrystallization and slurry purification to further improve the purity and quality of the crystalline form.

Recrystallization of the crystalline form in the present invention is achieved by methods which are generally used in synthetic organic chemistry such as (1) dissolving by heating followed by cooling, (2) a concentration method using solvent distillation after dissolving, and (3) precipitation of the crystalline form by dissolving in a good solvent followed by addition of a poor solvent thereto.

In cases where the crystalline form is dissolved in a solvent for recrystallization, dehydrochlorination may occur. In such cases, the crystalline form in the present invention can be obtained by adding hydrogen chloride or hydrochloric acid.

Slurry purification is a purification method wherein the crystalline form of a compound is suspended in an adequate solvent and is collected again by agitating the suspension.

Examples of solvents to be used for slurry purification of Crystalline form A in the present invention include esters such as methyl acetate and ethyl acetate; halogenated hydrocarbons such as methylene chloride and chloroform; aromatic hydrocarbons such as toluene and xylene; ethanol; water; aliphatic hydrocarbons such as hexane; ethers such as diisopropylether, diethylether and tetrahydrofuran; ketones such as acetone and methylethylketone; nitriles such as acetonitrile, and mixed solvents thereof. Preferably, water, methanol, tetrahydrofuran, or mixed solvents thereof are used. More preferably, water is used.

In cases where the crystalline form is suspended in a solvent for slurry purification, dehydrochlorination may occur. In such cases, Crystalline form A can be obtained by adding hydrogen chloride or hydrochloric acid.

Examples of solvents to be used for slurry purification of Crystalline form B in the present invention include ketones such as acetone and methylethylketone; esters such as methyl acetate and ethyl acetate; nitriles such as acetonitrile; halogenated hydrocarbons such as methylene chloride and chloroform; aromatic hydrocarbons such as toluene and xylene; alcohols such as ethanol and isopropanol; amides such as N,N-dimethylformamide; water; aliphatic hydrocarbons such as hexane; ethers such as tetrahydrofuran, diisopropylether and diethylether, and mixed solvents thereof. Preferably, water, methanol, tetrahydrofuran, or mixed solvents thereof are used. More preferably, water is used.

In cases where the crystalline form is suspended in a solvent for slurry purification, dehydrochlorination may occur. In such cases, Crystalline form B can be obtained by adding hydrogen chloride or hydrochloric acid.

The crystalline form which is obtained by recrystallization and slurry purification can be isolated and dried in a way similar to the methods mentioned above.

It is known that Compound (I) and pharmacologically acceptable salts thereof (particularly preferably, the hydrochloride salt thereof) have a significant ability of peroxisome proliferator-activated receptor (PPAR) γ activation, as is disclosed in Japanese Patent No. 3488099 (WO 99/18081, U.S. Pat. No. 6,432,993, European Patent No. 1022272) (Patent Literature 1), Japanese Patent Laid-Open No. 2003-238406 (WO 03/053440) (Patent Literature 2), Japanese Patent Laid-Open No. 2004-083574 (WO 2004/000356) (Patent Literature 3), Japanese Patent Laid-Open No. 2005-162727 (WO 2004/083167) (Patent Literature 4), WO 2007/091622 (Patent Literature 5) and the like.

In particular, WO 2007/091622 (Patent Literature 5) discloses that Compound (I) and the hydrochloride salt thereof are useful as anticancer pharmaceutical compositions for preventing or treating stomach cancer, colon cancer, lung cancer, breast cancer, pancreas cancer, kidney cancer, prostate cancer, medulloblastoma, rhabdomyosarcoma, Ewing's sarcoma, liposarcoma, multiple myeloma or leukemia.

More specifically, Test Example 1 in WO 2007/091622 (Patent Literature 5) discloses along with experimental data that the dihydrochloride of Compound (I) exerts a significant activity to suppress proliferation of any cancer cells including human stomach cancer cells, human breast cancer cells, small cell lung cancer, pancreas cancer cells, prostate cancer cells, kidney cancer cells, medulloblastoma, human sarcoma cells (rhabdomyosarcoma, Ewing's sarcoma, liposarcoma) and multiple myeloma.

Also, Test Example 2 in the same pamphlet (Patent Literature 5) discloses along with experimental data that the dihydrochloride of Compound (I) inhibits significantly proliferation suppressing activity in human leukemia cells.

In addition, Test Example 3 in WO 2007/091622 (Patent Literature 5) discloses that the dihydrochloride of Compound (I) exerts a significant antitumor activity in vivo against human colon cancer cell lines.

Moreover, Test Example 4 in the same pamphlet (Patent Literature 5) discloses that the administration of the dihydrochloride of Compound (I) in combination with an epidermal growth factor receptor (EGFR) inhibitor exerts a synergetic activity to suppress proliferation in cancer cells.

Also, Test Example 5 in the same pamphlet (Patent Literature 5) discloses that the dihydrochloride of Compound (I) exerts an antitumor activity against human non-small cell lung cancer, and that the administration of the same in combination with an epidermal growth factor receptor (EGFR) inhibitor exerts an enhanced antitumor activity.

Moreover, Test Example 6 in the same pamphlet (Patent Document 5) discloses that the administration of the dihydrochloride of Compound (I) in combination with a vascular endothelial growth factor receptor (VEGFR) inhibitor or a Raf kinase inhibitor exerts a synergetic activity to suppress proliferation in cancer cells.

Furthermore, Test Example 7 in the same pamphlet (Patent Document 5) discloses that the dihydrochloride of Compound (I) exerts an antitumor activity against human kidney cancer, and that the administration of the same in combination with a vascular endothelial growth factor receptor (VEGFR) inhibitor or a Raf kinase inhibitor exerts an enhanced antitumor activity.

Therefore, the crystalline form in the present invention is effective as a medicine, particularly as a PPAR γ activator, and is effective as an agent (anticancer pharmaceutical composition) for treating or preventing various cancers as described above.

In addition, Japanese Patent No. 3488099 (WO 99/18081, U.S. Pat. No. 6,432,993, European Patent No. 1022272) (Patent Literature 1) discloses that Compound (I) and pharmacologically acceptable salts thereof have a significant ability of peroxisome proliferator-activated receptor (PPAR) γ activation, a significant insulin resistance-improving action and a hypoglycemic action, and are also effective as agents for treating or preventing diabetes (in particular, type 2 diabetes). Therefore, the crystalline form in the present invention is effective as a pharmaceutical composition for preventing or treating diabetes (in particular, type 2 diabetes).

Moreover, the crystalline form in the present invention is effective as a pharmaceutical composition for preventing or treating cancers when occurring in conjunction with type 2 diabetes because it is an anticancer pharmaceutical composition as described above.

In cases where the crystalline form in the present invention is used as a medicine, particularly as a PPAR γ activator, an agent for treating or preventing cancers, or an agent for treating or preventing diabetes, the crystalline form can be administered either by itself or mixed with an appropriate and pharmacologically acceptable diluting agent or dilution agent and the like to form, for example, tablets, capsules, granules, powders or syrups for oral administration, or to form, for example, injectable solutions or suppositories for parenteral administration.

The preparations are manufactured by known methods using additives such as diluting agents (for example, sugars such as lactose, sucrose, glucose and sorbitol; derivatives of starch such as corn starch, potato starch, α-starch, dextrin and carboxymethylstarch; derivatives of cellulose such as crystalline cellulose, hydroxypropylmethyl cellulose, carboxymethyl cellulose, calcium carboxymethylcellulose and internally cross-linked sodium carboxymethylcellulose; gum arabic; dextran; pullulan; silicates such as synthetic aluminum silicate and magnesium aluminometasilicate; phosphates such as calcium phosphate; carbonates such as calcium carbonate; and hydrosulfates such as calcium sulfate), binders (for example, the above mentioned diluting agents; gelatin; polyvinylpyrrolidone; and macrogol), disintegrating agents (for example, the above mentioned diluting agents; chemically modified derivatives of starch or cellulose such as sodium croscarmellose, sodium carboxymethyl starch, cross-linked polyvinylpyrrolidone), lubricating agents (for example, talc; stearic acid; metallic stearates such as calcium stearate and magnesium stearate; colloid silica; veegum; waxes such as beeswax and whale wax; acidum boricum; glycol; carboxylic acids such as fumaric acid and adipic acid; sodium salts of carboxylic acids such as sodium benzoate; hydrosulfates such as sodium sulfate; leucine; lauryl sulfates such as sodium lauryl sulfate and magnesium lauryl sulfate; silicates such as light anhydrous silicic acid and silicic acid hydrates; derivatives of starch as described in the above mentioned diluting agents), fixing agents (for example, para-hydroxy benzoate esters such as methylparaben and propylparaben; alcohols such as chlorobutanol, benzyl alcohol and phenylethyl alcohol; benzalkonium chloride; phenols such as phenol and cresol; thimerosal; acetic acid anhydride; and sorbate), corrigents (for example, edulcorants, acidulants and fragrant materials which are generally used), suspending agents (for example, polysorbate 80 and sodium carboxymethyl cellulose), dilution agents, and solvents for preparation (for example, water, ethanol and glycerin).

The amount of the crystalline form of the present invention used may vary in accordance with the degree of symptoms, body weight and age of the patients (mammals, in particular humans) being administered, mode of administration and the like. For example, the recommended dose is in the range of a minimum of 0.001 mg/kg body weight (preferably 0.01 mg/kg body weight) to a maximum of 500 mg/kg body weight (preferably 50 mg/kg body weight) per dose for oral administration, and in the range of a minimum of 0.005 mg/kg body weight (preferably 0.05 mg/kg body weight) to a maximum of 50 mg/kg body weight (preferably 5 mg/kg body weight) per dose for intravenous administration. It is preferred to administer the agents once to several times per day in accordance to the degree of symptoms.

EXAMPLES

The present invention will now be described in connection with certain examples, test examples and preparation examples more specifically hereinafter.

Example 1

Crystalline Form A (1-1)
4.0 g of 5-(4-{[6-(4-amino-3,5-dimethylphenoxy)-1-methyl-1-H-benzimidazol-2-yl]methoxy}benzyl)-1,3-thiazolidine-2,4-dione hydrochloride obtained by a method similar to the method described in Example 8 of Japanese Patent No. 3488099 was suspended in a mixture of tetrahydrofuran (40 ml) and water (12 ml) at room temperature under a nitrogen atmosphere, and 2.4 g of 25% sodium hydroxide aqueous solution was dripped thereto to form a solution. The resulting solution was dripped to a suspension of activated carbon prepared under a nitrogen atmosphere (0.4 g) in tetrahydrofuran (12 ml) and the mixture was agitated for 20 minutes at the same temperature. After filtering off the activated carbon, the activated carbon was rinsed with 12 ml of tetrahydrofuran. The filtrate and the washing solution were combined, and 12 ml of water was added thereto. A mixed solution of 38% hydrochloric acid (3.2 g) and tetrahydrofuran (12 ml) was dripped to the resulting solution. The reaction mixture was agitated for 45 minutes. The mixture was cooled to 0° C. and further agitated for 2 hours. The obtained crystalline form was filtered off and was dried for 12 hours at a pressure of approximately 80 Pa and at 50° C. The crystalline form was left in the atmosphere for 3 hours to give 3.64 g of a crystalline form of a monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride.

(1-2)
2.0 g of the crystalline form obtained in (1-1) was suspended in 40 ml of water and the suspension was agitated for 20 minutes at 80° C. A mixture of 38% hydrochloric acid (1.1 g) and water (8.4 ml) was dripped thereto for 5 minutes at the same temperature. The reaction mixture was then agitated for 1 hour and was cooled to 40° C. The crystalline form was filtered off and rinsed with 6 ml of water to give a hygroscopic crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride. The obtained crystalline form was dried for 14 hours at a pressure of approximately 80 Pa and at 50° C. The crystalline form was let to sit in the atmosphere for 3 hours to give 1.83 g of the white crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride, wherein the crystalline form had the crystal form showing the diffraction pattern obtained by X-ray powder diffraction described in FIG. 1 (Crystalline fowl A).

(1-3)
FIG. 1 shows the diffraction pattern obtained by X-ray powder diffraction (Cu Kα, λ=1.54 angstroms) for the crystalline form obtained in (1-2). Table 1 shows the peaks which have relative intensities greater than or equal to 10 based on the intensity 100 of the largest peak based on the diffraction pattern described in FIG. 1. Numbers in FIG. 1 correspond to peak numbers in Table 1.

TABLE 1

| Peak number | 2θ | d value | Relative intensity |
|---|---|---|---|
| 1 | 8.18 | 10.80 | 25 |
| 2 | 8.58 | 10.30 | 11 |
| 3 | 12.52 | 7.06 | 100 |
| 4 | 14.90 | 5.94 | 13 |
| 5 | 14.98 | 5.91 | 14 |
| 6 | 15.28 | 5.79 | 46 |
| 7 | 16.02 | 5.53 | 28 |
| 8 | 16.32 | 5.43 | 43 |
| 9 | 17.56 | 5.05 | 14 |
| 10 | 18.88 | 4.70 | 24 |
| 11 | 19.38 | 4.58 | 11 |
| 12 | 20.00 | 4.44 | 38 |
| 13 | 20.48 | 4.33 | 25 |
| 14 | 21.24 | 4.18 | 30 |
| 15 | 21.94 | 4.05 | 17 |
| 16 | 22.36 | 3.97 | 34 |
| 17 | 22.72 | 3.91 | 42 |
| 18 | 23.16 | 3.84 | 24 |
| 19 | 23.48 | 3.79 | 17 |
| 20 | 24.14 | 3.68 | 40 |
| 21 | 24.62 | 3.61 | 18 |
| 22 | 25.12 | 3.54 | 16 |
| 23 | 25.54 | 3.48 | 76 |
| 24 | 27.50 | 3.24 | 19 |
| 25 | 28.72 | 3.10 | 14 |
| 26 | 28.98 | 3.08 | 14 |
| 27 | 29.74 | 3.00 | 17 |
| 28 | 30.06 | 2.97 | 31 |
| 29 | 30.68 | 2.91 | 17 |
| 30 | 31.76 | 2.82 | 10 |
| 31 | 32.80 | 2.73 | 12 |
| 32 | 33.20 | 2.70 | 14 |
| 33 | 35.50 | 2.53 | 11 |

Among these peaks, the peaks at interplanar spacings (d values) of 7.06, 5.79, 5.43, 4.44, 4.18, 3.97, 3.91, 3.68, 3.61, 3.48, 3.24 and 2.97 angstroms are particularly distinctive of Crystalline form A.

Figure 2:
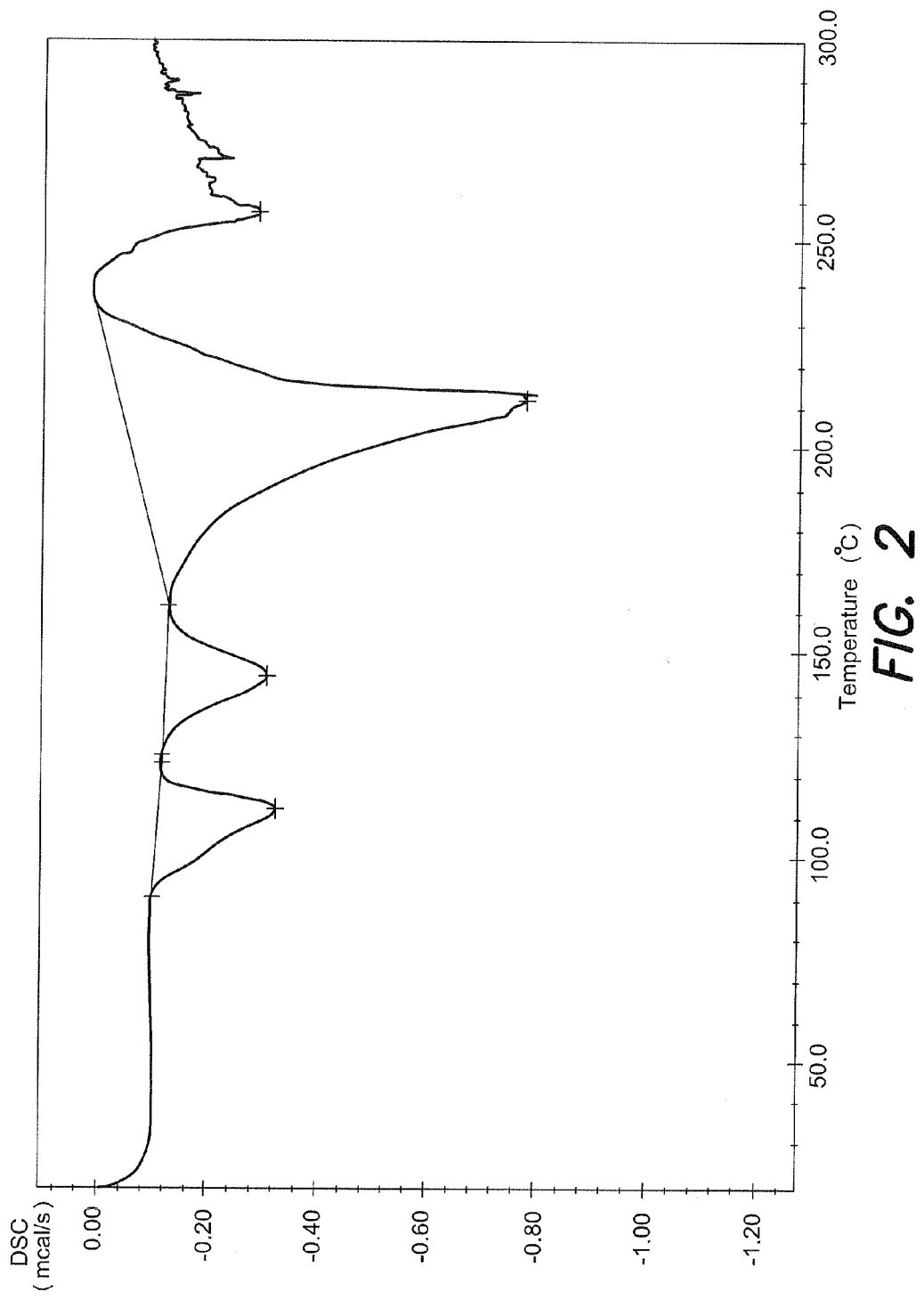
FIG. 2 is a differential thermal analysis (DSC) chart for Crystalline form A obtained in Example 1 when the temperature was raised at a rate of 5° C. per minute, the vertical axis showing a heating value per second (mcal/s) (or endothermic value when the value is negative), and the horizontal axis showing temperature (° C.)

(1-4)
FIG. 2 shows a differential thermal analysis (DSC) chart.

Example 2

Crystalline Form A (2-1)
2.0 g of 5-(4-{[6-(4-amino-3,5-dimethylphenoxy)-1-methyl-1-H-benzimidazol-2-yl]methoxy}benzyl)-1,3-thiazolidine-2,4-dione hydrochloride obtained by a method similar to the method described in Example 8 of Japanese Patent No. 3488099 was suspended in a mixture of tetrahydrofuran (20 ml) and water (6 ml) at room temperature under a nitrogen atmosphere, and 1.2 g of 25% sodium hydroxide aqueous solution was dripped thereto to form a solution. The resulting solution was dripped to a suspension of activated carbon prepared under a nitrogen atmosphere (0.2 g) in tetrahydrofuran (6 ml) and the mixture was agitated for 20 minutes at the same temperature. After filtering off the activated carbon, the activated carbon Was rinsed with 6 ml of tetrahydrofuran. The filtrate and the washing solution were combined, and 6 ml of water was added thereto. A mixed solution of 38% hydrochloric acid (1.6 g) and tetrahydrofuran (6 ml) was dripped to the resulting solution. The reaction mixture was agitated for 45 minutes. The mixture was cooled to 0° C. and further agitated for 2 hours. The obtained crystalline form was filtered off and rinsed with water to give a moist crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride.

(2-2)

The moist crystalline form obtained in (2-1) was suspended in 40 ml of water and the suspension was agitated for 20 minutes at 80° C. A mixture of 38% hydrochloric acid (1.1 g) and water (8.4 ml) was dripped thereto for 5 minutes at the same temperature. The reaction mixture was then agitated for 1 hour and was cooled to 40° C. The crystalline form was filtered off and rinsed with 6 ml of water to give a moist crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride. The obtained moist crystalline form was dried for 12 hours at a pressure of 4.3 kPa and at 50° C. to give a white crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride, wherein the crystalline form has the crystal form described in claim 2. The X-ray powder diffraction pattern and the differential thermal analysis chart of this crystalline form matched those for Crystalline form A obtained in Example 1.

Example 3

Crystalline Form A (3-1)

2.0 g of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride obtained by a method similar to the method described in Example 1-1 was suspended in 100 ml of water. The resulting suspension was refluxed for 2 hours. The reaction mixture was cooled to 0° C. and agitated for 1 hour. The obtained crystalline form was filtered off and rinsed with water. The obtained moist crystalline form was dried for 14 hours at a pressure of approximately 80 kPa and at 50° C. to give a crystalline form, wherein the proportion of 5-(4-{[6-(4-amino-3,5-dimethylphenoxy)-1-methyl-1-H-benzimidazol-2-yl]methoxy}benzyl)-1,3-thiazolidine-2,4-dione and hydrochloric acid was approximately 1 to 1.1.

(3-2)

The crystalline form obtained in (3-1) was suspended in 40 ml of water. A mixture of 38% hydrochloric acid (1.1 g) and water (8.4 ml) was dripped thereto for 5 minutes at 80° C. The reaction mixture was then agitated for 1 hour and was cooled to 0° C. The crystalline form was filtered off and rinsed with 6 ml of water to give a moist crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride. The obtained crystalline form was dried for 14 hours at a pressure of approximately 80 Pa and at 50° C. The crystalline form was left in the atmosphere for 3 days to give 1.83 g of a white crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride, wherein the crystalline form has the crystal form described in claim 2. The X-ray powder diffraction pattern and the differential thermal analysis chart of this crystalline form matched those for Crystalline form A obtained in Example 1.

Example 4

Crystalline Form A 4.0 g of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride obtained by a method similar to the method described in Example (1-1) were suspended in 160 ml of water under a nitrogen atmosphere, and 1.08 g of a 25% sodium hydroxide aqueous solution were dripped thereto at 80° C. The resulting mixture was agitated for 1 hour. The mixture was then cooled to 65° C., and a mixed solution of 38% hydrochloric acid (0.65 g) and water (4 ml) was dripped thereto at the same temperature. After adding 0.2 g of Crystalline form A thereto, the resulting solution was agitated for 1 hour, and a mixed solution of 38% hydrochloric acid (5.11 g) and water (31.6 ml) was dripped thereto for 1 hour at the same temperature. The reaction mixture was then agitated for 30 minutes at the same temperature, and was cooled to 40° C. The obtained crystalline form was filtered off and rinsed with a mixed solution of 38% hydrochloric acid (0.31 g) and water (12 ml). The obtained crystalline form was dried for 17 hours at a pressure of approximately 4.3 kPa and at 50° C. to give 3.98 g of Crystalline form A. The X-ray powder diffraction pattern and differential thermal analysis chart of this crystalline form matched those for Crystalline form A obtained in Example 1.

Example 5

Crystalline Form A 5.0 g of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride obtained by a method similar to the method described in Example (1-1) were suspended in 300 ml of water under a nitrogen atmosphere, and 1.94 g of 38% hydrochloric acid were dripped thereto. The resulting mixture was agitated at 95° C. to form a solution. A mixed solution of 38% hydrochloric acid (0.81 g) and water (5 ml) was dripped thereto at the same temperature. After adding 0.25 g of Crystalline form A thereto, the resulting mixture was agitated for 30 minutes, and a mixed solution of 38% hydrochloric acid (6.14 g) and water (38 ml) was dripped thereto for 2 hour at the same temperature. The reaction mixture was then agitated for 30 minutes, and was cooled to 40° C. The obtained crystalline form was filtered off and rinsed with a mixed solution of 38% hydrochloric acid (0.39 g) and water (15 ml). The obtained crystalline form was dried for 16 hours at a pressure of approximately 4.3 kPa and at 50° C. to give 5.01 g of Crystalline form A. The X-ray powder diffraction pattern and differential thermal analysis chart of this crystalline form matched those for Crystalline form A obtained in Example 1.

Example 6

Crystalline Form B (6-1)

2.5 g of the crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride obtained by the same method as the method described in Example 1 was suspended in 50 ml of methanol and was dissolved at 60° C. The resulting solution was cooled to 0° C. and agitated for 26 hours at the same temperature. The obtained crystalline form was dried for 16 hours at a pressure of approximately 80 Pa and at 50° C. to give an approximately hemihydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride.

(6-2)

Figure 3:
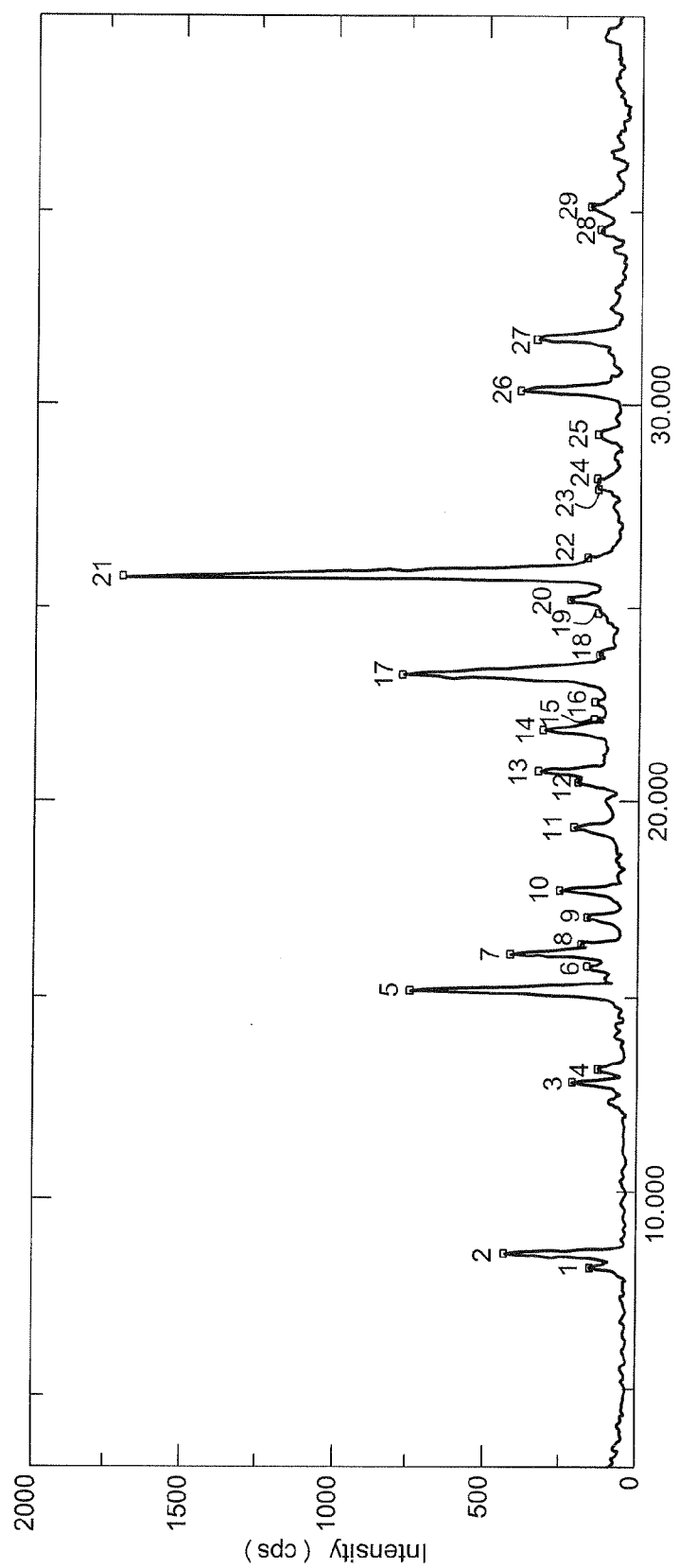
FIG. 3 is an X-ray powder diffraction pattern for Crystalline form B obtained in Example 3, the vertical axis showing diffraction intensity in units of counts/sec (cps), and the horizontal axis showing values of diffraction angle 2θ.

The crystalline form of the approximately hemihydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride obtained in (6-1) was let to sit for 19 hours at room temperature under approximately 100% relative humidity to give 1.6 g of the white crystalline form of the monohydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride, wherein the crystalline form had the crystal form showing the diffraction pattern obtained by X-ray powder diffraction described in FIG. 3 (Crystalline form B).

(6-3)

FIG. 3 shows the diffraction pattern obtained by X-ray powder diffraction (Cu Kα, λ=1.54 angstroms) for the crystalline form obtained in (6-2). Table 2 shows the peaks which have relative intensities greater than or equal to 7 based on the intensity 100 of the largest peak based on the diffraction pattern described in FIG. 3. Numbers in FIG. 3 correspond to peak numbers in Table 2.

TABLE 2

| Peak number | 2θ | d value | Relative intensity |
| --- | --- | --- | --- |
| 1 | 8.12 | 10.88 | 8 |
| 2 | 8.48 | 10.42 | 25 |
| 3 | 12.80 | 6.91 | 12 |
| 4 | 13.12 | 6.74 | 7 |
| 5 | 15.12 | 5.85 | 44 |
| 6 | 15.66 | 5.65 | 9 |
| 7 | 16.04 | 5.52 | 24 |
| 8 | 16.28 | 5.44 | 11 |
| 9 | 16.96 | 5.22 | 9 |
| 10 | 17.68 | 5.01 | 14 |
| 11 | 19.22 | 4.61 | 12 |
| 12 | 20.38 | 4.35 | 11 |
| 13 | 20.68 | 4.29 | 19 |
| 14 | 21.72 | 4.09 | 18 |
| 15 | 21.98 | 4.04 | 7 |
| 16 | 22.44 | 3.96 | 8 |
| 17 | 23.16 | 3.84 | 45 |
| 18 | 23.60 | 3.77 | 7 |
| 19 | 24.70 | 3.60 | 7 |
| 20 | 24.98 | 3.56 | 13 |
| 21 | 25.72 | 3.46 | 100 |
| 22 | 26.08 | 3.41 | 10 |
| 23 | 27.84 | 3.20 | 8 |
| 24 | 28.06 | 3.18 | 8 |
| 25 | 29.16 | 3.06 | 8 |
| 26 | 30.30 | 2.95 | 22 |
| 27 | 31.64 | 2.83 | 19 |
| 28 | 34.38 | 2.61 | 7 |
| 29 | 34.96 | 2.56 | 9 |

Among these peaks, the peaks at interplanar spacings (d values) of 10.42, 5.85, 5.52, 3.84, 3.46 and 2.95 angstroms are particularly distinctive of Crystalline form B.

(6-4)

Figure 4:
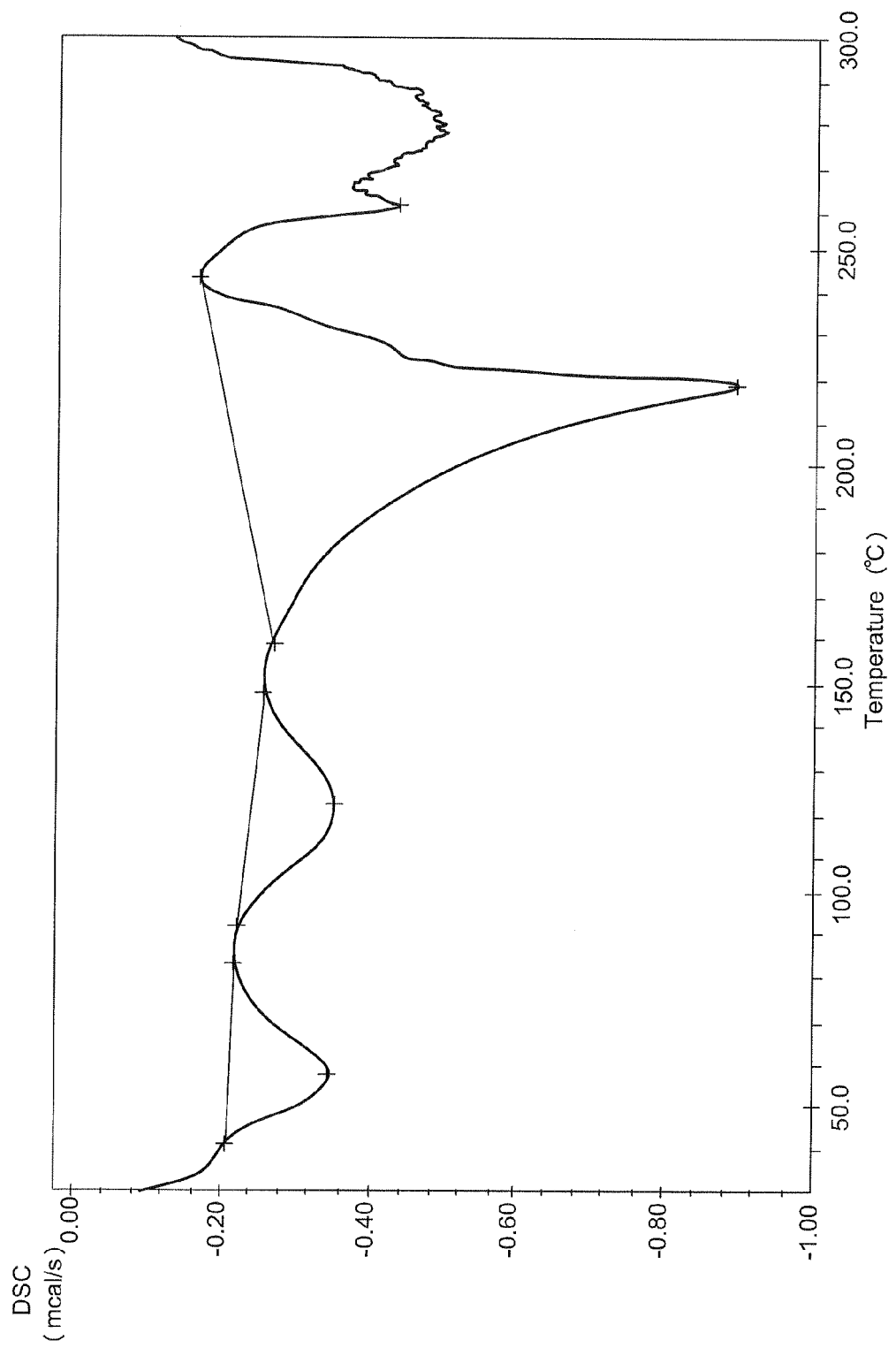
FIG. 4 is a differential thermal analysis (DSC) chart for Crystalline form B obtained in Example 3 when the temperature was raised at a rate of 5° C. per minute, the vertical axis showing a heating value per second (mcal/s) (or an endothermic value when the value is negative) and the horizontal axis showing temperature (° C.)

FIG. 4 shows a differential thermal analysis (DSC) chart.

Comparative Example 1

Figure 5:
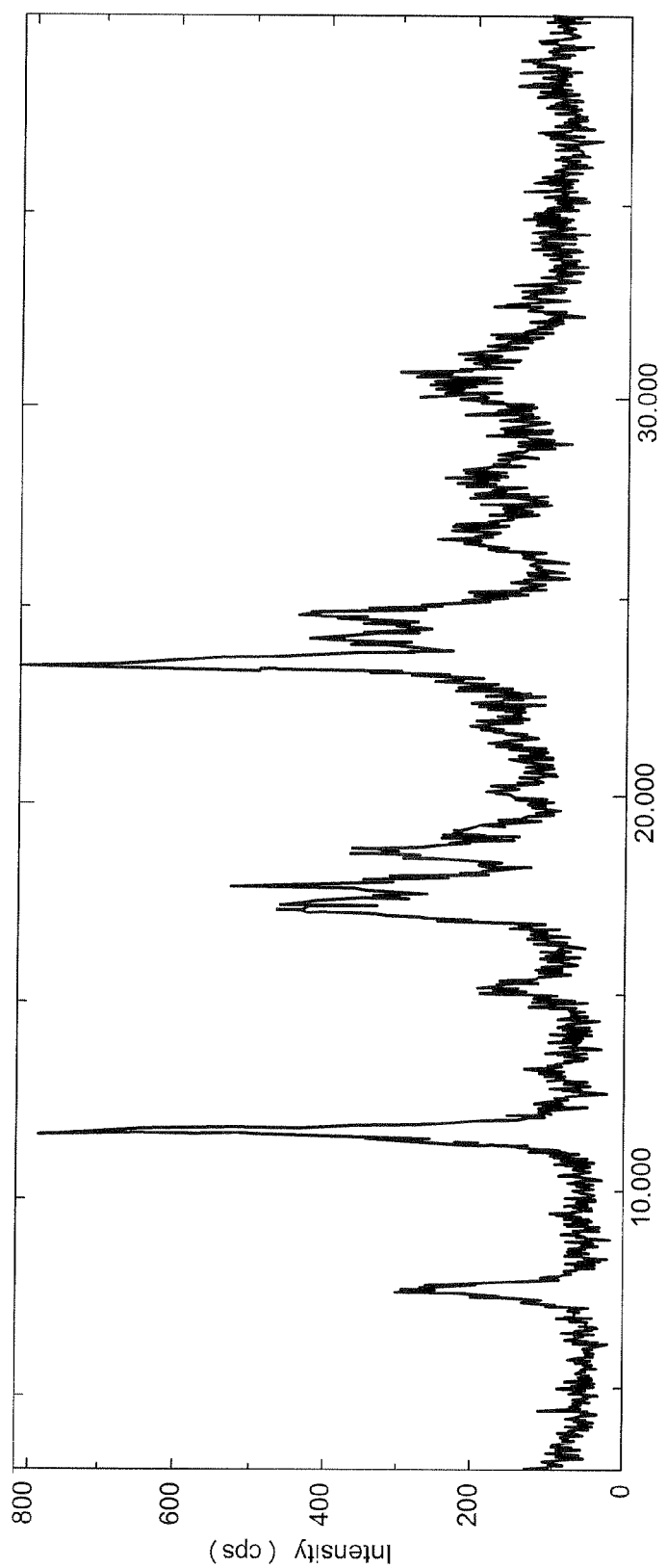
FIG. 5 is the X-ray powder diffraction pattern for the compound obtained in Comparative Example 1. In the figure, the vertical axis shows diffraction intensity in units of counts/sec (cps), and the horizontal axis shows values of diffraction angle 2θ.

5-(4-{[6-(4-amino-3,5-dimethylphenoxy)-1-methyl-1-H-benzimidazol-2-yl]methoxy}benzyl)-1,3-thiazolidine-2,4-dione hydrochloride was manufactured by the method described in Example 8 of Japanese Patent No. 3488099. The obtained compound exhibited a faint red purple color. FIG. 5 shows the diffraction pattern obtained by X-ray powder diffraction (Cu Kα, λ=1.54 angstroms) for this compound.

TEST EXAMPLES

Test Example 1

Content Measurement

The contents of Crystalline form A obtained in Example 1 and the compound obtained in Comparative Example 1 (the hydrochloride salt of 5-(4-{[6-(4-amino-3,5-dimethylphenoxy)-1-methyl-1-H-benzimidazol-2-yl]methoxy}benzyl)-1,3-thiazolidine-2,4-dione obtained by a method similar to the method described in Example 8 of Japanese Patent No. 3488099, which was used as a material as described in Example 1, this is also the case in Test Examples 2-4) were measured by the analysis method below by using HPLC.

0.01 mol/ml ammonium acetate buffer was prepared by adding a 0.01 mol/ml ammonium acetate aqueous solution to a 0.01 mol/ml acetic acid aqueous solution and adjusting to pH=4.5.

Water, acetonitrile and methanol were mixed at a proportion of 55:40:5 by volume to give a sample dissolution solution.

0.2 g of isoamyl 4-hydroxybenzoate were dissolved in the sample dissolution solution to bring the total volume to 200 ml to give an internal standard solution.

Approximately 0.03949 g of the standard of the 5-(4-{[6-(4-amino-3,5-dimethylphenoxy)-1-methyl-1-H-benzimidazol-2-yl]methoxy}benzyl)-1,3-thiazolidine-2,4-dione dihydrochloride monohydrate were precisely measured, transferred to a 200 ml volumetric flask, and dissolved in the sample dissolution solution to bring the total volume to 200 ml. 5 ml of the resulting solution were precisely measured, transferred to a 50 ml volumetric flask, and 10 ml of the internal standard solution were precisely added thereto. The sample dissolution solution was further added thereto to bring the total volume to 50 ml to give a standard solution.

Approximately 0.01 g of the subject for content measurement was precisely measured, transferred to a 10 ml volumetric flask, and approximately 2.5 ml of dimethylsulfoxide were added thereto to bring it into solution. The sample dissolution solution was further added thereto to bring the total volume to 10 ml. 2 ml of the resulting solution were precisely measured, transferred to a 100 ml volumetric flask, and 20 ml of the internal standard solution were precisely added thereto. The sample dissolution solution was further added thereto to bring the total volume to 100 ml to give a sample solution.

Contents were measured under the conditions below.
Detector: UV absorptiometer (wavelength: 290 nm)
Column: Waters Corporation, Symmetry C18 (4.6 mm×100 mm)
Column temperature: 40° C.
Mobile phase: 0.01 mol/ml ammonium acetate buffer-acetonitrile (3:2)
Flow rate: 1 ml/min (Under the present conditions, 5-(4-{[6-(4-amino-3,5-dimethylphenoxy)-1-methyl-1-H-benzimidazol-2-yl]methoxy}benzyl)-1,3-thiazolidine-2,4-dione showed a retention time of approximately 8 minutes.)
Injection amount of the standard solution and the sample solution: 10 μl
Peak area measurement range: Approximately 20 minutes after the start of the injection.

Contents are given by the following formula.

$$\text{Content}(\%)=(Q_T \times W_S \times F_P) \div (Q_S \times W_T)$$

wherein
weighing amount of the standard at the time of preparation of the standard solution (g): $W_S$;
weighing amount of the sample at the time of preparation of the sample solution (g): $W_T$;
purification coefficient of the standard: $F_P$;
the value of the peak area for the standard divided by the peak area for the internal standard in the chromatogram of the standard solution: $Q_S$; and
the value of the peak area for the sample divided by the peak area for the internal standard in the chromatogram of the sample solution: $Q_T$.

The obtained measurement results are shown in Table 3.

TABLE 3

|  | Compound obtained in Comparative Example 1 | Crystalline form A obtained in Example 1 |
|---|---|---|
| Content (%) | 87.0 | 96.5 |

It is shown that Crystalline form A in the present invention has a significantly enhanced purity compared to 5-(4-{[6-(4-amino-3,5-dimethylphenoxy)-1-methyl-1-H-benzimidazol-2-yl]methoxy}benzyl)-1,3-thiazolidine-2,4-dione hydrochloride (the compound of Comparative Example 1), which had been conventionally obtained, and, at the same time, the method for obtaining Crystalline form A in the present invention has a high purification effect.

Test Example 2

Impurity

The impurity content ratio in Crystalline form A obtained in Example 1 and the compound obtained in Comparative Example 1 was measured by the analysis method below by using HPLC.

The term impurity content ratio here represents the ratio of the integration area for all peaks whose peak area ratios are measured as equal or above 0.01%, excluding the peak for Compound (I) and the peak which is detected when injecting a solvent alone, to the peak area for Compound (I) under the below described measurement conditions.

Moreover, the term individual impurity represents a peak area ratio for a peak whose peak area ratio is measured as equal or above 0.01%, excluding the peak for Compound (1) and the peak which is detected when injecting a solvent alone.

0.01 mol/ml ammonium acetate buffer was prepared by adding a 0.01 mol/ml ammonium acetate aqueous solution to a 0.01 mol/ml acetic acid aqueous solution and adjusting to pH=4.5.

Water and acetonitrile were mixed at a proportion of 3:2 by volume to give a sample dissolution solution.

0.01 g of the subject for measurement was precisely measured, transferred to a 20 ml brown volumetric flask, and approximately 1 ml of dimethylsulfoxide was added thereto to form a solution. The total volume was then brought to 20 ml to give a sample solution.

1 ml of the sample solution was precisely measured, transferred to a 100 ml brown volumetric flask. The sample dissolution solution was added thereto to bring the total volume to 100 ml to give a standard solution.

Measurements were conducted under the conditions below.

HPLC Measurement Conditions (1)
Detector: UV absorptiometer (wavelength: 230 nm)
Column: Waters Corporation, XTerra $RP_{18}$ (4.6 mm×150 mm)
Column temperature: 40° C.
Mobile phase: 0.01 mol/ml ammonium acetate buffer-acetonitrile (65:35)
Flow rate: 1 ml/min (Under the present conditions, Compound (1) showed a retention time of approximately 25 minutes.)
Injection amount of the standard solution and the sample solution: 10 μl
Area measurement range: 70 minutes after the start of the injection.

HPLC Measurement Conditions (2)
Detector: UV absorptiometer (wavelength: 230 nm)
Column: Waters Corporation, XTerra $RP_{18}$ (4.6 mm×150 mm)
Column temperature: 40° C.
Mobile phase: 0.01 mol/ml ammonium acetate buffer-acetonitrile (56:44)
Flow rate: 1 ml/min (Under the present conditions, Compound (1) showed a retention time of approximately 8 minutes.)
Injection amount of the standard solution and the sample solution: 10 μl
Area measurement range: 70 minutes after the peak which elutes next to the peak whose retention time relative to Compound (I) is 1.48.

Impurity content ratios were calculated by the following formula.

Impurity content ratio(%)=[The sum of the individual impurities above 0.01% measured under HPLC Measurement Conditions(1)]+[The sum of the individual impurities above 0.01% measured under HPLC Measurement Conditions(2)]

wherein
the sum of the individual impurities above 0.01% measured under HPLC Measurement Conditions (1) (%)=$A_{i1}/A_{S1}$; and
the sum of the individual impurities above 0.01% measured under HPLC Measurement Conditions (2) (%)=$A_{i2}/A_{S2}$
wherein the above formula
the peak area for Compound (I) in the standard solution measured under HPLC Measurement Conditions (1): $A_{S1}$;
the peak area for individual impurities above 0.01% measured under HPLC Measurement Conditions (1): $A_{i1}$;
the peak area for compound (1) in the standard solution measured under HPLC Measurement Conditions (2): $A_{S2}$; and
the peak area for individual impurities above 0.01% measured under HPLC Measurement Conditions (2): $A_{i2}$.

The obtained measurement results are shown in Table 4.

TABLE 4

| Measurement method | Relative retention time [h] | Impurity in compound obtained in Comparative Example 1 (%) | Impurity in Crystalline form A in Example 1 (%) |
|---|---|---|---|
| HPLC Measurement conditions (1) | 0.13 | 0.10 | — |
|  | 0.189 | 0.14 | — |
|  | 0.192 | 0.24 | 0.02 |
|  | 0.35 | 0.51 | 0.24 |
|  | 0.88 | 1.06 | <0.01 |
|  | 1.15 | 1.57 | 0.68 |

TABLE 4-continued

| Measurement method | Relative retention time [h] | Impurity in compound obtained in Comparative Example 1 (%) | Impurity in Crystalline form A in Example 1 (%) |
|---|---|---|---|
|  | 1.19 | 0.10 | — |
|  | 1.71 | 0.10 | 0.05 |
|  | Others | 0.75 | 0.11 |
| HPLC measurement conditions (2) | 2.06 | 0.18 | 0.05 |
|  | 3.98 | 0.20 | 0.09 |
|  | Others | 0.30 | 0.14 |
| Impurity content ratio [%] |  | 5.25 | 1.38 |

It is shown that the method for obtaining Crystalline form A in the present invention has a high impurity removal effect.

Test Example 3

Residual Solvent

Residual solvents in Crystalline form A and Crystalline form B obtained in Examples, and in the compound obtained in Comparative Example 1 were measured by gas chromatography in accordance with the analysis method below.

(1) Method for Preparing Samples of Crystalline Form A and Crystalline Form B

Dimethylformamide and water were mixed at a proportion of 7:3 by volume to give a dilute solution.

1 ml of t-butyl alcohol was precisely measured, transferred to a 100 ml volumetric flask, and dissolved to the dilute solution to bring the total volume to 100 ml. 10 ml of the resulting solution were precisely measured, transferred to a 500 ml volumetric flask, and the dilute solution was added thereto to bring the total volume to 500 ml to give an internal standard solution.

2 ml of tetrahydrofuran, 2 ml of diisopropyl ether, 2 ml of methanol, 2 ml of acetic ethyl, 2 ml of acetic acid, and 2 ml of 1,4-dioxane were precisely measured, transferred to a 250 ml volumetric flask, and the internal standard solution was added thereto to bring the total volume to 250 ml. 1 ml of the resulting solution was precisely measured, transferred to a 100 ml volumetric flask, and the internal standard solution was added thereto to bring the total volume to 100 ml. 6 ml out of 100 ml of the resulting solution were precisely measured, and transferred to a 20 ml headspace vial container. The vial container was closed using a rubber plug, and stoppered tightly by twisting and closing an aluminum cap to give a standard solution.

0.1 g of the sample for measurement was precisely measured, transferred to a 20 ml headspace vial container, and 6 ml of the internal standard solution were precisely added thereto. The vial container was closed using a rubber plug, and stoppered tightly by twisting and closing an aluminum cap. The sample was completely dissolved while shaking in a water bath at a temperature ranging from 60 to 70° C. to give a sample solution.

(2) Method for Preparing Sample of the Compound in Comparative Example 1

1 ml of t-butyl alcohol was precisely measured, transferred to a 100 ml volumetric flask, and dissolved to chlorobenzene to bring the total volume to 100 ml. 10 ml of the resulting solution were precisely measured, transferred to a 500 ml volumetric flask, and chlorobenzene was added thereto to bring the total volume to 500 ml to give an internal standard solution.

2 ml of tetrahydrofuran, 2 ml of diisopropyl ether, 2 ml of methanol, 2 ml of acetic ethyl, 2 ml of acetic acid, and 2 ml of 1,4-dioxane were precisely measured, transferred to a 250 ml volumetric flask, and the internal standard solution was added thereto to bring the total volume to 250 ml. 1 ml of the resulting solution was precisely measured, transferred to a 100 ml volumetric flask, and the internal standard solution was added thereto to bring the total volume to 100 ml. 6 ml out of 100 ml of the resulting solution were precisely measured, and transferred to a 20 ml headspace vial container. The vial container was closed using a rubber plug, and stoppered tightly by twisting and closing an aluminum cap to give a standard solution.

0.1 g of the sample for measurement was precisely measured, transferred to a 20 ml headspace vial container, and 6 ml of the internal standard solution and 100 μl of tributylamine were precisely added thereto. The vial container was closed using a rubber plug, and stoppered tightly by twisting and closing an aluminum cap. The sample was completely dissolved while shaking in a water bath at the temperature ranging from 60 to 70° C. to give a sample solution.

(3) Test Condition

Residual levels of solvents were measured under the test conditions below.

Detector: Hydrogen flame ionization detector
Column: J&W Inc., DB-624 (0.53 mm×30 m)
Column temperature: 40° C. (hold 5 minutes)→Temperature rise at a rate of 10° C./min→260° C. (hold 3 minutes)
Temperature of sample vaporizing chamber: 250° C.
Detector temperature: 300° C.
Carrier gas: Helium
Column flow rate: 5 ml/min (Column flow rate was adjusted to obtain a retention time of approximately 7 minutes for tetrahydrofuran.)
Split ratio: 1:10
Sample injection method: Split method
Area measurement range: 20 minutes (4) Operating Condition for the Headspace Apparatus Equilibrium temperature inside the vial (oven temperature): 85° C.
Equilibrium time inside the vial: 15 minutes
Injection line temperature
　Sample loop temperature: 95° C.
　Transfer line temperature: 110° C.
Carrier gas: Helium
Vial pressure time: 0.20 minutes
Vial pressure: Approximately 10 kPa
Sample loop fill time: 0.15 minutes
Sample loop equilibrium time: 0.05 minutes
Injection time: 1.0 minute
Sample injection amount: 1 ml (5) Method for Calculating Residual Solvent Residual level of each solvent is given by the following formula.

$$\text{Residual level of each solvent (ppm)} = (2 \times D \times Q_T \times 6 \times 10000000) \div (Q_S \times 25000 \times W)$$

wherein
weighing amount of the sample (g): $W$;
density of each solvent (g/ml): $D$;
the ratio of the area for each solvent in the standard solution to the peak area for the internal standard substance: $Q_S$; and
the ratio of the area for each solvent in the sample solution to the peak area for the internal standard substance: $Q_T$ The obtained measurement results are shown in Table 5.

TABLE 5

| Solvent name | Residual level in compound obtained in Comparative Example 1 (ppm) | Residual level in Crystalline form A obtained in Example 1 (ppm) | Residual level in Crystalline form B obtained in Example 6 (ppm) |
| --- | --- | --- | --- |
| Methanol | 25 | ND | 1385 |
| Ethanol | 1713 | ND | ND |
| Hexane | ND | ND | ND |
| Diisopropyl ethyl | ND | ND | ND |
| Acetic ether | 9297 | ND | ND |
| Tetrahydrofuran | ND | 271 | ND |
| Acetic acid | 3892 | ND | ND |
| 1,4-dioxane | ND | ND | ND |
| Total | 14926 | 271 | 1385 |

It is shown that there is only one kind of residual solvent in Crystalline form A and Crystalline form B in the present invention, and the amounts are extremely low.

Test Example 4

Color Tone

Approximately 1 g of the test substance was placed on a sheet of white paper to observe its color tone. The test results are shown in Table 6.

TABLE 6

| | Compound obtained in Comparative Example 1 | Crystalline form A obtained in Example 1 |
| --- | --- | --- |
| Color tone | Faint red purple | White |

It is shown that the method for obtaining Crystalline form A in the present invention has a high decolorization effect.

Test Example 5

Solubility Test

Solubilities of Crystalline form A and Crystalline form B of Compound (I) in a simulated gastric fluid were measured by the method below (free body conversion).

10 times concentrated Liquid 1 used for the disintegration test of the Japanese Pharmacopoeia (purchased from Kanto Chemical Co., Inc.) was diluted 10-fold with purified water to give a simulated gastric fluid. Approximately 80 mg of the crystalline form for measurement were precisely measured, transferred to a 25 ml volumetric flask, and dissolved in methanol to bring the total volume to 25 ml. 2 ml of the resulting solution were transferred to a 50 ml volumetric flask, and the simulated gastric fluid was added thereto to bring the total volume to 50 ml to give a standard solution.

By using an elution testing machine NTR-6100A (Toyama Sangyo Co., Ltd.), approximately 100 mg of the subject crystalline form were added to 500 ml of the simulated gastric fluid at 37° C., and agitated with a paddle (250 rpm). After 60 minutes, samples were taken from the test solution. The absorbance of the standard solution and test solution samples was measured at 289 nm and 360 nm by using a UV visible spectrophotometer.

Solubility is calculated by the following formula.

$$\text{Solubility}(\mu g/ml) = \{(A_{S289} - A_{S360}) \times W_S \times 1000 \times 502.58\} \div \{(A_{T289} - A_{T360}) \times 625 \times 593.52\}$$

wherein weighing amount of the crystalline form used for the preparation of the standard solution (mg): $W_S$;

absorbance of the standard solution at 289 nm: $A_{S289}$;

absorbance of the standard solution at 360 nm: $A_{S360}$;

absorbance of the test solution at 289 nm: $A_{T289}$;

absorbance of the test solution at 360 nm: $A_{T360}$;

molecular weight of the dihydrochloride monohydrate of Compound (I): 593.52; and molecular weight of the free body of Compound (I): 502.58

The obtained test results are shown in Table 7.

TABLE 7

| | Crystalline form A | Crystalline form B |
| --- | --- | --- |
| Solubility (μg/ml) | 76.92 | 155.25 |

Crystalline form A and Crystalline form B in the present invention showed sufficient solubility as a pharmaceutical ingredient.

PREPARATION EXAMPLES

Preparation Example 1

Capsule

After 5 g of Crystalline form A obtained in Example 1 are mixed with 115 g of lactose, 58 g of corn starch and 2 g of magnesium stearate in a V-type mixing machine, 180 mg of the mixture is filled in a capsule No. 3 to give the capsules thereof.

Preparation Example 2

Tablet

After 5 g of Crystalline form A obtained in Example 1 is mixed with 90 g of lactose, 34 g of corn starch, 20 g of crystalline cellulose and 1 g of magnesium stearate in a V-type mixing machine, the mixture is compressed in a tabletting machine to give tablets weighing 150 mg each.

Preparation Example 3

Suspension

A dispersion medium is prepared, wherein methylcellulose is diffused and dissolved in purified water. Crystalline form A obtained in Example 1 is placed in a mortar after weighing and kneaded well while adding thereto the above mentioned dispersion medium in small portions. Purified water is added to prepare 100 g of the suspension.

The invention claimed is:

1. A crystalline form of a hydrate of a dihydrochloride of 5-(4-{[6-(4-amino-3,5-dimethylphenoxy)-1-methyl-1-H- benzimidazol-2-yl]methoxy}benzyl)-1,3-thiazolidine-2,4-dione represented by the following formula:

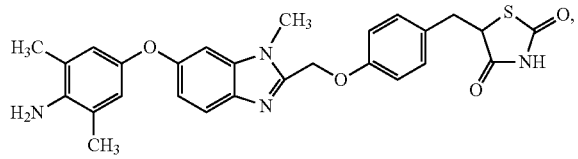 [SMILES: Cc1cc(Oc2ccc3nc(COc4ccc(CC5SC(=O)NC5=O)cc4)n(C)c3c2)cc(C)c1N]

wherein the crystalline form shows main peaks at interplanar spacings of 10.42, 5.85, 5.52, 3.84, 3.46 and 2.95 angstroms in X-ray powder diffraction obtained with Cu Kα line radiation (wavelength λ=1.54 angstroms).

2. A method of manufacturing the crystalline form according to claim 1, comprising recrystallizing a hydrate of 5-(4-{[6-(4-amino-3,5-dimethylphenoxy)-1-methyl-1-H-benzimidazol-2-yl]methoxy}benzyl)-1,3-thiazolidine-2,4-dione dihydrochloride from methanol and subjecting the hydrate to moisture absorption at a temperature of 0 to 50° C. in a 20 to 50% relative humidity range until the weight remains always constant.

3. A method of treating diabetes in a mammal comprising administering to a mammal in need thereof a pharmaceutically effective amount of the crystalline form according to claim 1.

4. The method according to claim 3, wherein the mammal is a human.

5. The method according to claim 4, wherein the diabetes is type 2 diabetes.

6. The method according to claim 3, wherein the method is for treating a human.

7. A method of treating a cancer in a mammal, wherein the cancer is stomach cancer, colon cancer, lung cancer, breast cancer, pancreatic cancer, kidney cancer, prostate cancer, medulloblastoma, rhabdomyosarcoma, Ewing's sarcoma, liposarcoma, multiple myeloma or leukemia, comprising administering to a mammal in need thereof a pharmaceutically effective amount of the crystalline form according to claim 1.

8. The method according to claim 7, wherein the mammal is a human.

9. The method according to claim 7, wherein the method is for treating a human.

10. A method of treating diabetes in a mammal comprising administering to a mammal in need thereof a pharmaceutically effective amount of a crystalline form of a hydrate of a dihydrochloride of 5-(4-{[6-(4-amino-3,5-dimethylphenoxy)-1-methyl-1-H-benzimidazol-2-yl]methoxy}benzyl)-1,3-thiazolidine-2,4-dione represented by the following formula:

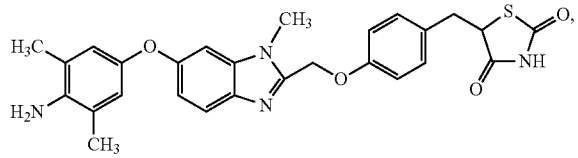

wherein the crystalline form shows main peaks at interplanar spacings of 7.06, 5.79, 5.43, 4.44, 4.18, 3.97, 3.91, 3.68, 3.61, 3.48, 3.24 and 2.97 angstroms in X-ray powder diffraction obtained with Cu Kα line radiation (wavelength λ=1.54 angstroms).

11. The method according to claim 10, wherein the mammal is a human.

12. The method according to claim 11, wherein the diabetes is type 2 diabetes.

13. The method according to claim 10, wherein the method is for treating a human.

14. A method of treating cancer in a mammal, wherein the cancer is stomach cancer, colon cancer, lung cancer, breast cancer, pancreatic cancer, kidney cancer, prostate cancer, medulloblastoma, rhabdomyosarcoma, Ewing's sarcoma, liposarcoma, multiple myeloma or leukemia, comprising administering to a mammal in need thereof a pharmaceutically effective amount of a crystalline form of a hydrate of a dihydrochloride of 5-(4-{[6-(4-amino-3,5-dimethylphenoxy)-1-methyl-1-H-benzimidazol-2-yl]methoxy}benzyl)-1,3-thiazolidine-2,4-dione represented by the following formula:

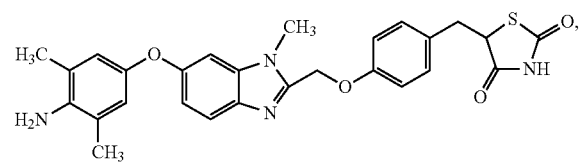 [SMILES: Cc1cc(Oc2ccc3nc(COc4ccc(CC5SC(=O)NC5=O)cc4)n(C)c3c2)cc(C)c1N]

wherein the crystalline form shows main peaks at interplanar spacings of 7.06, 5.79, 5.43, 4.44, 4.18, 3.97, 3.91, 3.68, 3.61, 3.48, 3.24 and 2.97 angstroms in X-ray powder diffraction obtained with Cu Kα line radiation (wavelength λ=1.54 angstroms).

15. The method according to claim 14, wherein the mammal is a human.

16. The method according to claim 14, wherein the method is for treating a human.

17. The method according to claim 15, wherein the cancer is colon cancer.

18. The method according to claim 15, wherein the cancer is breast cancer.

19. The method according to claim 15, wherein the cancer is pancreatic cancer.

20. The method according to claim 15, wherein the cancer is kidney cancer.

21. The method according to claim 15, wherein the cancer is prostate cancer.

22. The method according to claim 15, wherein the cancer is liposarcoma.

23. A method of preparing a PPAR$_\gamma$ activator comprising mixing an effective amount of the crystalline form according to claim 1 and a pharmacologically acceptable additive.

* * * * *